US005685758A

United States Patent [19]
Paul et al.

[11] Patent Number: 5,685,758
[45] Date of Patent: Nov. 11, 1997

[54] HOT MELT ADHESIVE COMPOSITIONS WITH IMPROVED WICKING PROPERTIES

[75] Inventors: Charles W. Paul, Madison; Matthew L. Sharak, Franklin Park; Bing Wu, Somerville; Lydia Wagner, Bedminster; Quinn Tong, Belle Mead; Gary Raykovitz, Flemington, all of N.J.

[73] Assignee: National Starch and Chemical Investment Holding Corporation, Wilmington, Del.

[21] Appl. No.: 631,390

[22] Filed: Apr. 12, 1996

[51] Int. Cl.$^6$ .................................................... A61F 13/15
[52] U.S. Cl. ............................ 442/409; 428/355 EN; 442/411; 442/414
[58] Field of Search .................. 428/355, 261, 428/355 EN; 442/409, 411, 414

[56] References Cited

U.S. PATENT DOCUMENTS

| | | | |
|---|---|---|---|
| 4,189,338 | 2/1980 | Ejima et al. | 156/167 |
| 4,234,655 | 11/1980 | Kunimune et al. | 428/374 |
| 4,269,888 | 5/1981 | Ejima et al. | 428/296 |
| 4,434,261 | 2/1984 | Brugel et al. | 524/109 |
| 4,458,042 | 7/1984 | Espy | 524/14 |
| 4,548,845 | 10/1985 | Parsons et al. | 428/40 |
| 4,655,877 | 4/1987 | Horimoto et al. | 162/146 |
| 5,066,711 | 11/1991 | Colon et al. | 524/556 |
| 5,169,890 | 12/1992 | Eadara et al. | 524/271 |
| 5,322,876 | 6/1994 | Sasaki et al. | 524/366 |
| 5,342,861 | 8/1994 | Raykovitz | 523/111 |
| 5,391,601 | 2/1995 | Teeters | 524/270 |
| 5,414,039 | 5/1995 | Watson | 524/502 |
| 5,436,287 | 7/1995 | Watson | 524/272 |
| 5,441,998 | 8/1995 | Teeters | 524/270 |
| 5,456,982 | 10/1995 | Hansen et al. | 428/370 |
| 5,472,785 | 12/1995 | Stobbie | 428/423.1 |
| 5,541,246 | 7/1996 | Dandreaux | 524/272 |

FOREIGN PATENT DOCUMENTS 47-43308  5/1972  Japan.

*Primary Examiner*—Jenna Davis
*Attorney, Agent, or Firm*—Jane E. Gennaro

[57] ABSTRACT

A nonwoven disposable article is constructed using adhesive compositions containing 1 to 25% of a surfactant, which causes the adhesive composition to exhibit a contact angle of 90° or less and a reduction in surface tension of less than or equal to about 35–40 dynes/cm, giving improved wicking capabilities to the nonwoven.

5 Claims, No Drawings

HOT MELT ADHESIVE COMPOSITIONS WITH IMPROVED WICKING PROPERTIES

FIELD OF THE INVENTION

This invention relates to hot melt adhesives for bonding nonwoven fabrics and tissues.

BACKGROUND OF THE INVENTION

A nonwoven fabric is an interlocking network of synthetic or naturally occurring fibers, or a combination of the two, in which the individual fibers are mechanically, chemically, or thermally bonded to each other. Tissue is a closely related material in which the individual fibers may or may not be bonded to one another. The fabric or tissue is characterized by flexibility, porosity and integrity. Nonwovens are used commercially for a variety of applications including insulation, packaging, household wipes, surgical drapes, medical dressings, and disposable articles, such as, diapers, adult incontinent products and sanitary napkins.

In many of the end use applications it is necessary to adhere the nonwoven or tissue to another substrate or component. The second substrate may be another nonwoven, tissue, or an unrelated material, such as a polyethylene film. Commonly, hot melt adhesives are employed to bond the assembly together. Hot melt adhesives allow for cost and time efficient manufacturing since there is no evaporation step necessary as is the case for water based or solvent based adhesive systems. For nonwoven applications, suitable hot melt adhesives must possess good flexibility (or hand); no staining or bleed through; suitable viscosity, set speed and open time to function on commercially available equipment; and finally, acceptable thermal aging properties.

Another desired property for hot melt adhesives, especially important in disposable diaper, sanitary napkin, and bed pad constructions, is the ability of the hot melt adhesive to transmit liquid or moisture from the nonwoven fibers into the superabsorbent or fluff core substrates. This property, referred to as strike through, is desirable to draw the moisture away from the body and into the absorbent core as quickly as possible after the nonwoven is wetted.

Many hot melt adhesives are hydrophobic and repel moisture, rather than drawing it through the adhesive and into the absorbent core. It is known to use fluorchemical surfactants in some hot melt adhesives to provide improved strike through without reducing the absorbency speed or capacity of the absorbing material. In addition to their use as construction adhesives, hot melt adhesives may be used to bind or reinforce the nonwoven fibers together. These hot melts adhesives may also be formulated to provide improved strike through by fluorosurfactants. However, fluorosurfactants are costly, absorb through the skin, and persist in the body. These limitations make them unsuitable for disposable nonwovens that are in direct contact with the body.

SUMMARY OF THE INVENTION

We have discovered that, when used at the proper level, the addition of a variety of hydrocarbon and silicone surfactants to conventional olefin-containing hot melts for use in nonwovens confers the unexpected benefits of improved fluid acquisition rates and spreading (wicking), and resistance to high humidity and direct water immersion.

This invention is a disposable article containing at least one nonwoven or tissue layer bonded to another nonwoven, tissue, or polyolefin film layer using a hot melt adhesive composition consisting of (a) 10 to 80 weight percent, preferred 40 to 60 weight percent, of an olefin containing polymer, (b) 10 to 70 weight percent, preferred 30 to 60 weight percent of a compatible tackifying resin, c) 0 to 20% plasticizer, (d) 0 to 2% stabilizer, (e) 0 to 25% wax, and (f) 1–25% of a surfactant, which surfactant will cause the adhesive composition to exhibit a contact angle of 90° or less and a reduction in surface tension of less than about 35–40 dynes/cm, preferably less than or equal to 35 dynes/cm, preferably 30 dynes/cm, more preferably 20 dynes/cm.

When a droplet of liquid is placed on a uniform, perfectly flat, solid surface, its shape and the length of time that it holds its shape are determined by three interfacial tension forces: the force of the solid surface, the surface tension of the liquid, and the force at the solid/liquid interface. The angle that the tangent (edge) of the liquid droplet makes with the solid surface is a measured value relative to those combined vector forces. In general, the smaller the contact angle, $\Theta$, the greater the tendency of the liquid droplet to lose its shape and spread. The addition of surfactants to the liquid causes a reduction of surface tension of the droplet.

In the case of hot melt adhesives for use in the construction of nonwoven applications, the addition of surfactant to the adhesive causes a decrease in the contact angle, $\Theta$, of any fluid against the adhesive. As a result the presence of the surfactant makes the adhesive more effective in transmitting fluids through the adhesive layer and into the core of the superabsorbent material. The same result would be obtained if the surfactant were added to a hot melt adhesive used for binding or reinforcing the nonwoven fibers. At the same time that the contact angle of the fluid is reduced, the surface tension is also reduced, but this lessens the capability of the fluid to wick through to the core of the nonwoven. Thus, in preparing the adhesives for this application, a balance must be achieved in the type and amount of surfactant used to provide the optimum performance. It has been found that optimum performance is obtained by the addition of a surfactant to the hot melt adhesives of a type and in an amount so that the fluid passing through the disposable exhibits a contact angle of less than 90°, and a reduction in surface tension of less than about 35–40 dynes/cm, preferably less than or equal to 35 dynes/cm.

The improved hot melt adhesive composition used in the disposable articles of this invention helps prevent leakage from the absorbent core and allows the use of thinner absorbent core substrates.

The preferred surfactants are ethoxylates of mono-alcohols and are present in the adhesive in an amount from 1 to 25 weight percent. Ethoxylates of mono-alcohols are the reaction products of the polymerization of ethylene oxide initiated at the —OH site of the alcohol.

The addition of the surfactant increases the hydrophilic character of the hot melt adhesive and improves its strike through properties rather than causing it, as compared to conventional hot melts, to act as a barrier to the liquid transmission.

DETAILED DESCRIPTION OF THE INVENTION

The surfactants utilized herein will be any of those surfactants, which when added in sufficient amount to the adhesive composition will impart improved wicking properties to the adhesive without causing a loss in adhesive properties.

Particularly preferred are the higher crystalline type surfactants, such as Unithox 480, a product of Petrolite Specialty Polymers Group, Tulsa, Okla.

Typically, the surfactants will be used in amounts of 1 to 25%, preferably 5 to 15% by weight, but the exact preferred range will depend on the individual adhesive system.

Suitable surfactants include nonionic, anionic, and silicone surfactants. Exemplary nonionic surfactants are:

ethoxylates of (i) $C_1$–$C_{18}$, preferred $C_8$–$C_9$ alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mole ethoxylate of octyl phenol; (ii) alkyl $C_8$–$C_{60}$ mono-alcohols, such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/propylene oxide block copolymers having a Mn of 200 to 3000 available from BASF; and benzoates formed by partial condensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical.

Suitable anionic surfactants are:

$C_8$–$C_{60}$ alkyl ethoxylate sulfonates, $CH_3$—$(CH_2)_{11-14}$—$(O$—$CH_2CH_2)_3$—$SO_3^-Na^+$, such as, Avenel S30, available from PPG Industries;

alkyl $C_8$–$C_{60}$ sulfonates, such as, Rhodapon UB ($C_{12}$—$SO_3^-Na^+$) available from Rhone Poulenc;

and alkyl/aromatic sulfonates, such as are represented by the structure

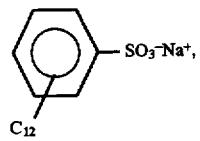

and sold under the tradename Calsoft.

Suitable silicone surfactants are ethoxylates or propoxylates of polydimethyl siloxane, having a number average molecular weight of 500 to 10,000, preferably 600 to 6000, such as are sold under the tradenames Silwet L-77, L-7605, and L-7500 available from OSi Specialties, Danbury, Conn.; and product 193 from Dow Corning.

The preferred surfactants are those with lower molecular weights because these have increased compatibility in the adhesive formulations. The maximum acceptable molecular weight depends on the type of surfactant and the other ingredients in the adhesive formulation.

The surfactant may be added to any olefin-containing polymers commonly used for disposable applications.

Suitable olefin-containing polymers are those in which ethylene is polymerized with 15 to 45% by weight of copolymerizable monomers such as vinyl acetate, N-butyl acrylate, propylene, methyl acrylate, methyl acrylic acid, acrylic acid, metallocene catalyzed ethylene based polymers and the like, as well as any mixtures thereof.

Additional suitable polymers are pure homopolymers or copolymers of the following monomers: olefins, such as ethylene, propylene, butene, hexene octene, or other alpha-olefins; vinyl monomers, such as vinyl acetate, vinyl propionate, vinyl butyrate, vinyl hexanoate; acrylic monomers, such as acrylic acid and methacrylic acid, methacrylic acid esters, hydroxy ethyl acrylate, and the like.

Preferred polymers are ethylene/vinyl acetate copolymers such as those obtainable from Dupont under the Elvax tradename. The preferred range for the vinyl acetate will be in the range of 18%–40% by weight, with 33% most preferred. Also preferred are polyolefin polymers such as those obtainable under the Vestoplast tradename from Hüls.

Other adhesive compositions may be prepared according to the invention using, as a base polymer, amorphous polyolefins or blends thereof. Amorphous polyolefins are made by the atactic polymerization of polypropylene. Polymerization occurs in the presence of a catalyst comprising a coordination complex of a transition metal halide with an organometallic compound. The solid amorphous polypropylene has a softening point of about 150° C. and a Brookfield viscosity at 190° C. of 1,000 to 50,000 cps. Suitable commercial products include Eastman Chemical's P 1010. Copolymers of amorphous polypropylene and ethylene (APE), or butene (APB), or hexene (APH), are suitable as a base polymer, as are terpolymers of propylene, butene and ethylene (APBE). Suitable commercially available products include those sold under the tradenames: Rextac 2315 from Rexene (APE); Rextac 2730 from Rexene (APB); Vestoplast 750 and 708 from Hüls (APBE).

Blends of any of the above base materials, such as blends of ethylene vinyl acetate and atactic polypropylene may also be used to prepare the hot melt adhesive compositions.

In all cases, the adhesives are formulated with tackifying resins, plasticizers, waxes and/or other conventional additives in varying amounts as are known to those skilled in the art.

The tackifying resins useful in the adhesive compositions can be any compatible hydrocarbon resins, synthetic polyterpenes, rosin esters, natural terpenes, and the like. More particularly, and depending upon the particular base polymer, the useful tackifying resins include (1) natural and modified rosins, for example, gum rosin, wood rosin, tall oil rosin, distilled rosin, hydrogenated rosin, dimerized rosin, and polymerized rosin; (2) glycerol and pentaerythritol esters of natural and modified rosins, for example, the glycerol ester of pale wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, for example, styrene/terpene and alpha methyl styrene/terpene; (4) polyterpene resins having a softening point, as determined by ASTM method E28-58T, of 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; and hydrogenated polyterpene resins; (5) phenolic modified terpene resins and hydrogenated derivatives thereof, for example, the resin product resulting from the condensation, in an acidic medium, of a bicyclic terpene and a phenol; (6) aliphatic petroleum hydrocarbon resins having a Ball and Ring softening point of 70° to 135° C.; the latter resins resulting from the polymerization of monomers primarily consisting of olefins and di-olefins; and the hydrogenated aliphatic petroleum hydrocarbon resins; (7) aromatic petroleum hydrocarbon resins and the hydrogenated derivatives thereof; (8) alicyclic petroleum hydrocarbon resins and the hydrogenated derivatives thereof; and (9) aromatic/aliphatic or alicyclic hydrocarbon resins, such as those sold under the trademarks ECR 149B and ECR 179A by Exxon Chemical Company. Mixtures of two or more of the above described tackifying resins may be required for some formulations.

Various plasticizing or extending oils may also be present in the composition in amounts of up to about 20%, preferably 0 to 15%, by weight in order to provide wetting action and/or viscosity control. The above broadly includes not only the usual plasticizing oils but also use of olefin oligomers and low molecular weight polymers, as well as vegetable and animal oils and their derivatives. Petroleum derived oils that may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, or the like, having average molecular weights between about 350 and about 10,000. Vegetable and animal oils include glyceryl esters of the usual fatty acids and polymerization products thereof.

Also useful as plasticizers are polar synthetic compounds, such as the aliphatic and aromatic polyester plasticizers available from C. P. Hall Co., Stow, Ohio. Amides phosphate esters, sulfonamides, and phthalates are also suitable at varying levels.

Various petroleum derived waxes may also be used in amounts less than about 25% by weight of the composition in order to impart fluidity in the molten condition of the adhesive and flexibility to the set adhesive, and to serve as a wetting agent for bonding cellulosic fibers. The term "petroleum derived wax" includes both paraffin and microcrystalline waxes having melting points within the range of 130° to 225° F. as well as synthetic waxes such as low molecular weight polyethylene or Fisher-Tropsch waxes.

An antioxidant or stabilizer may also be included in the adhesive compositions in amounts of up to about 3% by weight. Among the applicable antioxidants or stabilizers are high molecular weight hindered phenols and multifunctional phenols, such as sulfur and phosphorous-containing phenols. Representative hindered phenols include: 1,3,5-trimethyl 2,4,6-tris (3,5-di-tert-butyl-4-hydroxy-benzyl) benzene; pentaerythritol tetrakis-3(3,5-di-tert-butyl-4-hydroxyphenyl)-propionate; n-octadecyl-3,5-di-tert-butyl-4-hydroxyphenol)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octyl-thio)-1,3,5-triazine; di-n-octadecyl 3,5-di-tert-butyl-4-hydroxybenzyl-phosphonate; 2-(n-octylthio)-ethyl 3,5-di-tert-butyl-4-hydroxy-benzoate; and sorbitol hexa[3-(3,5-di-tert-butyl-4-hydroxyphenyl)-propionate].

Other additives conventionally used in hot melt adhesives to satisfy different properties and meet specific application requirements also may be added, and include fillers, pigments, flow modifiers, dyestuffs, etc., which may be incorporated in minor or larger amounts into the adhesive formulation, depending on the purpose.

These hot melt adhesives may be prepared using techniques known in the art. Typically, the adhesive compositions are prepared by blending the components in the melt at a temperature of about 100° to 200° C. until a homogeneous blend is obtained, approximately two hours. Various methods of blending are known and any method that produces a homogeneous blend is satisfactory. The resulting adhesives are characterized in that they have a viscosity of 50,000 cP or less at the application temperature of 350° F. (177° C.) or less. The viscosity as used herein is a Brookfield viscosity measured using a Brookfield viscometer model No. DV-II with spindle no. 27 at 10 rpm.

The resulting adhesives of the present invention are characterized by their ability to provide a durable bond to a nonwoven or tissue article and otherwise meet the unique requirements of the application (including flexibility, non-staining, and machinable viscosity). The adhesives described herein also possess exceptional thermal stability, which distinguishes them from other moisture sensitive technologies. Further, their hydrophilic natures facilitate ready transmission of the fluid throughout the construction.

The adhesive product can be applied to a substrate such as a nonwoven article or tissue by a variety of methods including coating or spraying in an amount sufficient to cause the article to adhere to another substrate, such as tissue, nonwoven, or other conventionally employed substrates, such as polyolefin films.

The following examples illustrate the compositions of suitable hot melt adhesives, and the improvement to their wicking properties as a result of the incorporation of the described surfactants.

EXAMPLES

Sample adhesives were prepared and tested for water contact angle, surface tension reduction, and rate of wicking.

Raw Materials

The following raw materials were used:

Elvax 460, an ethylene/vinyl acetate (EVA) copolymer from DuPont containing 18% vinyl acetate (VA), with a melt flow index (MFI) of 2.5 (dg/min at 190° C. using a 2.2 kg weight) (the MFI for the following are measured the same);

Elvax 265, an EVA from DuPont containing 28% VA, 3 MFI;

Elvax 200W, an EVA from DuPont containing 28% VA, 2500 MFI;

Elvax 140W, an EVA from DuPont containing 33% VA, 400 MFI;

Elvax 210W, an EVA from DuPont containing 28% VA, 400 MFI;

Elvax 40W, an EVA from DuPont containing 40% VA, 51 MFI;

Unitac 100 L, a rosin ester tackifier available from Union Camp;

Macol DNP-10, a 10 mole ethoxylate of dinonyl phenol from PPG;

Nirez V2040 HM, a terpene phenolic tackifier available from Arizona Chemical;

Zonatac 85L and 105L, styrenated terpenes with softening points at 85° and 105° C., respectively, from Arizona Chemical;

Irganox 1010, a hindered phenol anti-oxidant available from Ciba-Geigy;

Triton X-100, a 10 mole ethoxylate of octyl phenol available from Union Carbide;

Surfonic DNP-100, a 10 mole ethoxylate of dinonyl phenol available from Huntsman;

L12-8, an 8 mole ethoxylate of dodecanol available from Huntsman;

Pycal 94, a 4 mole ethoxylate of phenol available from ICI;

Unithox 480, an ethoxylated C$_{30}$ mono-ol with a molecular weight of 2250 g/mole, available from Petrolite Specialty Polymers Group, Tulsa, Okla.;

Escorez 2520, a liquid aliphatic/aromatic C$_5$-C$_9$ resin available from Exxon Chemical;

Nirez M85NS, an aromatic modified polyterpene available from Arizona Chemical;

Nirez V2040HM, a terpene phenolic tackifier available from Arizona Chemical;

Newtac 300, a phenol modified polyterpene available from Arizona Chemical;

AC-400, an EVA wax with 13% VA and a viscosity at 140° C. of 595 cP, available from Allied-Signal;

Macol DNP-10, a 10 mole ethoxylate of dinonyl phenol from PPG Industries;

Avenel S30, an anionic surfactant, sodium sulfonated 3 mole ethoxylate of a C$_{12-15}$ mono-ol, available from PPG industries;

Rhodapon UB, an anionic surfactant, sodium lauryl sulfate, available from Rhone Poulenc;

Silwet L-77, L-7605 and L-7500, silicone surfactants available from OSI Specialties;

Pluronic F38, F68, P65, P85, P61 and L44, ethylene oxide/propylene oxide block copolymer surfactants available from BASF;

Unitac R98L, hydrogenated rosin ester available from Union Camp; and

Jordapon CI, a prilled form of sodium cocoyl isethionate from PPG Industries;

Aerosol MA80, a sodium hexyl sulfo-succinate from Cytec Industries; and

Naugard HM22, an aromatic amine/hindered phenol blend available from Uniroyal;

Eastotac, a dicyclopentadiene-based tackifier available from Eastman Chemical Co.

Example I

Sample adhesive compositions for construction of nonwoven articles were formulated from the above listed raw materials to the following compositions in parts by weight (PBW). The adhesive used as a control contained no surfactant.

|  | PBW |
| --- | --- |
| Control | |
| Elvax 140W | 45.0 |
| Zonatac 85L | 55.0 |
| Irganox 1010 | 0.3 |
| Sample A | |
| Elvax 200W | 7.0 |
| Elvax 40W | 5.0 |
| Elvax 140 W | 34.5 |
| Sylvatac 4100 | 19.0 |
| Escorez 2520 | 5.0 |
| AC-400 | 7.0 |
| L12-8 | 10.0 |
| Nirez M85NS | 16.0 |
| Sample B | |
| Elvax 200W | 7.0 |
| Elvax 40W | 5.0 |
| Elvax 140 W | 34.5 |
| Sylvatac 4100 | 19.0 |
| Escorez 2520 | 5.0 |
| AC-400 | 7.0 |
| Surfonic DNP-100 | 10.0 |
| Naugard HM22 | 0.3 |
| Zonatac 85L | 16.0 |
| Sample C | |
| Elvax 200 | 12.5 |
| Elvax 140W | 33.0 |
| Escorez 2520 | 4.5 |
| AC-400 | 6.0 |
| Zonatac 85L | 16.0 |
| Irganox 1010 | 0.3 |
| Macol DNP-10 | 10.0 |
| Samples D–N | |
| Elvax 140W | 50.0 |
| Zonatac 105L | 40.0 |
| Irganox 1010 | 0.5 |
| Surfactant | 10.0 |
| Sampes O–T | |
| Elvax 140W | 40.0 |
| Zonatac 105L | 50.0 |
| Irganox 1010 | 0.5 |
| Surfactant | 10.0 |

The surfactant in each of the samples D–T was varied as reported here by tradename:

| Sample | Surfactant | Sample | Surfactant |
| --- | --- | --- | --- |
| D | Triton X-100 | E | Macol DNP10 |
| F | 193 Surfactant | G | Avanel S30 |
| H | Jordapon Cl | I | Rhodapon UB |
| J | Aerosol MA80 | K | CalSoft |
| L | Silwet L-77 | M | Silwet L-7605 |
| N | Silwet L-7500 | | |
| O | Pluronic F38, 80% EO, MW 4500 | | |
| P | Pluronic F68, 80% EO, MW 9000 | | |
| Q | Pluronic P65, 50% EO, MW 3600 | | |
| R | Pluronic P85, 50% EO, MW 4800 | | |
| S | Pluronic P61, 10% EO, MW 2000 | | |
| T | Pluronic L44, 40% EO, MW 2200 | | |

The following procedures were used to test the samples.

Contact Angle Test

The contact angle is measured with the use of a goniometer, which has a microsyringe for dispensing accurate droplet sizes and a camera for photographing the angle of the liquid drop as it meets the surface of the solid. The contact angle is measured as the angle between The substrate and the tangent of the liquid drop (at the interface). The lower the angle, the more effective the coating is in transmitting (wicking) the liquid through the discontinuous adhesive layer.

Surface Tension

The water surface tension was measured using the Dunuoy ring method. Two grams of adhesive were placed in a clean 110 ml glass jar with a 5 cm inner diameter, melted in a 135° C. oven, and then cooled to room temperature. Twenty ml of 0.85% saline solution was added to the dish. The surface tensions of the pure saline solution and of the saline solution after 15 minutes exposure to the adhesive were measured using a KRUS K-14 tensiometer. The difference in the surface tensions were recorded as the surface tension reduction (STR).

Fluid Wicking Area

Samples of substrate, 3 inches wide by 10 inches long, including the adhesive coverage area, are taped to Plexiglass 3 inches from the top on the front, and wrapped around to 3 inches from the top on the back side. The samples are conditioned at 72° F./50% RH for 24 hours. A one liter beaker is filled to the 200 mL level, with 0.9% saline solution dyed red. The sample is placed into the beaker and the fluid is allowed to rise for 2 minutes, at which time the sample is removed from the beaker and the total wicking area is calculated (within 10 seconds).

The results of these tests are tabulated here and show that the addition of the surfactant causes an increase in the surface wicking area (samples C and E); causes the contact angle to be less than 90° (samples A–G, K, and M–T); and results in a surface tension reduction of about 35 dynes/cm or less.

| Sample | Contact Angle | Surface Tension Reduction | Fluid Wicking Area |
|---|---|---|---|
| Control | 110–112° | | 20.2 in² |
| A | 61° | | |
| B | <17° | | |
| C | <30° | | 21.5 in² |
| D | <30° | | |
| E | <30° | 28 | 21.2 in² |
| F | 54 | 32 | |
| G | 47 | 35 | |
| H | | 36 | |
| I | | 6 | |
| J | | 26 | |
| K | 65 | 22 | |
| L | | 37 | |
| M | 76 | 28 | |
| N | 73 | 30 | |
| O | 46 | 12 | |
| P | 41 | 17 | |
| Q | 42 | 26 | |
| R | 39 | 24 | |
| S | 49 | 26 | |
| T | 54 | 22 | |

Adhesive sample E was chosen as the representative sample for comparison to the control adhesive in tests to measure bond strength after exposure to humidity or to soaking in water. The adhesives were tested according to the following test procedures.

Humidity Test

Sample nonwoven fabrics were adhered or bonded to a polyethylene substrate using the above adhesive compositions at a temperature of 149° C. (300° F.), applied by a coater machine at 450 ft/min. and 2.66 g/m². Two sets of adhesive bonds were prepared for each adhesive and conditioned for three days: one set at ambient conditions, and the second at 49° C. (120° F.), 90% RH. A rubber-based construction adhesive with no surfactant was used as a control. After conditioning, the bonds were pulled on an Instron machine at 12 in/min crosshead speed, 2 in/min chart speed in a 180° T peel mode. The average peel mode of four trials was recorded; if there was bond failure, the type of failure was recorded instead of peel value.

Soak Test

Poly to nonwoven bonds were made on samples as described above, and also with a rubber based adhesive containing 28 parts by weight of styrene/isoprene/styrene, 56 parts by weight of a partially saponified rosin, and 16 parts by weight of the surfactant sold under the trademark Macol DNP-10. Bonds were made using the coater machine at 300° F., 450 ft/min. and 4.5°/m². For each adhesive, one set of bonds was stored in ambient conditions. A second set was soaked in room temperature deionized water for one hour, after which the water was drained and the bonds immediately tested. Bonds were pulled on the Instron machine at 12 in/min crosshead speed, 2 in/min chart speed in a 180° T peel mode. The average peel mode of four trials was recorded; if there was bond failure, the type of failure was recorded instead of peel value.

The results of both tests are reported in the following Table.

| | | Bond Strengths | |
|---|---|---|---|
| Conditions | Sample E | Control adh. | Rubber-based adh. with surfactant |
| Ambient | 207 g | 275 g | |
| 72 hrs. 120° F. 90% R.H. | 182 g | 331 g | |
| Failure Mode | 3 | 2 | |
| Ambient - dry | 152 g | 264 g | 348 g |
| Soaking - wet | 189 g | 292 g | no bond |
| Failure Mode - dry | 1 | 1 | 1 |
| Failure Mode - wet | 2 | 1 | not testable |

The code for the failure modes is the following:

1. Adhesive failure from nonwoven, with some fiber pullout.
2. Adhesive failure from nonwoven, no visible fiber pullout.
3. Adhesive failure from poly.
4. Cohesive failure mostly to poly.

The bond held with the rubber based adhesive with surfactant fell apart during the soak test.

The samples conditioned by soaking may have greater bond strength values than the samples conditioned in ambient temperature and humidity due to softening of the adhesive or matting of the nonwoven.

The results of this test show that excellent poly/nonwoven bonds can be obtained, which resist high humidity and direct water immersion, despite their low contact angle.

Example II

Benefits of Crystalline Surfactants

This example used crystallizable surfactants to achieve low water contact angle and low water STR. The crystallinity of the surfactant significantly decreases the mobility of the surfactant and thus results in low water STR. Depending on the molecular structure, the crystalline site can be either the hydrophobic portion or the hydrophilic portion of the surfactant, or both. The improvement in water STR is shown in the table below. The formulations give components in parts by weight in parentheses.

| Formulation | Crystallizability of the surfactant | Contact Angle | STR (dynes/cm) | Viscosity (135° C.) |
|---|---|---|---|---|
| Example E | no | <30 | 28 | 10,500 cps |

-continued

| Formulation | Crystalliz-ability of the surfactant | Contact Angle | STR (dynes/cm) | Viscosity (135° C.) |
|---|---|---|---|---|
| Example U<br>Elvax 210W (40)<br>Zonatac 105L (50)<br>Irganox 1010 (0.5)<br>Unithox 480 (10) | yes (both hydrophilic and hydrophobic portions) | <30 | 14 | 9,000 cps |
| Example V<br>Elvax 140W (40)<br>Zonatac 105L (50)<br>Irganox 1010 (0.5)<br>Unithox 480 (10) | yes (both hydrophilic and hydrophobic portions) | <30 | 14 | 9,500 cps |

The crystallization of the surfactant in Examples U and V is confirmed by DSC measurements performed with a Perkin-Elmer DSC-7. The sample was heated to 150° C., held for 5 minutes at that temperature, and cooled to room temperature at 10° C./min. The sample was then reheated at 10° C./min., and this run was used to determine the crystallinity of the surfactant in the formulation. The heat of fusion and melting point of the sample were determined on the reheat cycle. By itself, Unithox 480 material exhibits a melting peak at 56° C. and a heat of fusion of 112 J/g. In the adhesive formulations U and V a melting peak at 53° C. is observed superimposed on that of the EVA base polymers. This peak indicates that the surfactant is recrystallizing in the formulations (thus, is crystallizable).

Example III

These are examples of high viscosity, high strength, faster setting adhesives suitable for use as binder fibers when comingled with other fibers in a nonwoven fabric. The compositions are given in parts by weight in the following table in parts by weight, and the identity of the raw materials can be found earlier in this specification.

| | Adhesive Compositions | | | | | | |
|---|---|---|---|---|---|---|---|
| | AA | BB | CC | DD | EE | FF | GG |
| Components | | | | | | | |
| Elvax 460 | 50 | 50 | 50 | 50 | 50 | | |
| Elvax 265 | | | | | | 50 | 50 |
| Unitac 100L | 40 | 20 | | | | 40 | |
| Zonatac 105L | | | | | 40 | | 40 |
| Eastotac H100 | | | 20 | | | | |
| Nirez V2040HM | | 20 | 20 | 40 | | | |
| DNP-10 | 10 | 10 | 10 | 10 | 10 | 10 | 10 |
| Irganox 1010 | | | | | 0.5 | 0.5 | 0.5 |
| Viscosity (P) at 200° C. | 975 | 1030 | 1045 | 1185 | 8870 | 945 | 910 |

For samples AA–DD, 100 g of each sample was held at 177° C. (350° F.) in a glass jar for 24 hours. No phase separation occurred for any sample. A solidified puddle of each adhesive (about 5 cm in diameter by 1.5 mm thick) was held at 38° C. (100° F./95% RH) overnight. No exudation of surfactant occurred. A drop of water was place gently by pipette on the surface of each adhesive. Adhesives BB–DD showed contact angles of 60°–80°, which fell as the drop stood. Adhesive AA gave almost instantaneous wet out of the water drop. On a larger scale, 1000 lbs of adhesive AA was prepared in a sigma-blade mixer, fed molten into an extruder, and pelletized underwater.

All three samples EE–GG were readily wet out by a drop of water. The lower vinyl acetate content of adhesive EE makes it a harder product compared to sample GG.

In summary, the results show that these adhesives may be successfully used to form nonwoven disposable products. It will be apparent that various changes and modifications may be made in the embodiments of the invention described above, without departing from the scope of the invention, as defined in the appended claims, and it is intended therefore, that all matter contained in the foregoing description shall be interpreted as illustrative only and not limitative of the invention.

We claim:

1. A disposable article containing an absorbent core bound together or reinforced with hot melt adhesive fibers consisting of (a) 10 to 80 weight percent of an olefin containing polymer, (b) 10 to 70 weight percent of a compatible tackifying resin, c) 0 to 20% plasticizer, (d) 0 to 2% stabilizer, (e) 0 to 25% wax, and (f) 1 to 25% of a surfactant, which surfactant will cause the adhesive composition to exhibit a contact angle of 90° or less and a reduction in surface tension of less than about 40 dynes/cm.

2. The disposable article according to claim 1 in which the surfactant is an ethoxylate of $C_1$–$C_{18}$ alkyl or dialkyl phenol; an ethoxylate of an alkyl $C_8$–$C_{60}$ mono-alcohol; an ethylene oxide/propylene oxide block copolymer having a Mn of 200 to 3000; a benzoate formed by partial condensation of benzoic acid with a hydrophilic di- or mono-ol having less than 1000 Mn; a $C_8$–$C_{60}$ alkyl ethoxylate sulfonate; an alkyl $C_8$–$C_{60}$ sulfonate; an alkyl/aromatic sulfonate; or an ethoxylate or propoxylate of polydimethyl siloxane having a number average molecular weight of 500 to 10,000.

3. The disposable article according to claim 1 in which the surfactant is a crystallizable surfactant.

4. The disposable article according to claim 1 in which the olefin containing polymer is present in an amount of 40 to 60 weight percent.

5. The disposable article according to claim 1 in which the tackifying resin is present in an amount of 30 to 60 weight percent.

* * * * *